United States Patent [19]

Coenen

[11] Patent Number: 4,642,151

[45] Date of Patent: Feb. 10, 1987

[54] APPARATUS AND METHOD FOR APPLYING TRANSVERSE ELASTIC SEGMENTS

[75] Inventor: Joseph D. Coenen, Outagamie County, Wis.

[73] Assignee: Kimberly-Clark Corporation, Neenah, Wis.

[21] Appl. No.: 760,190

[22] Filed: Jul. 29, 1985

[51] Int. Cl.⁴ .............................................. B32B 31/08
[52] U.S. Cl. ................................... 156/164; 156/229; 156/265; 156/494; 156/519; 156/552
[58] Field of Search ................................ 156/518–522, 156/250, 264, 265, 164, 229, 494, 552, 225; 493/212, 377, 379

[56] References Cited

U.S. PATENT DOCUMENTS

| | | | |
|---|---|---|---|
| 2,157,556 | 5/1939 | Menschner | 156/552 X |
| 2,276,745 | 3/1942 | Smith | 156/552 X |
| 2,760,414 | 8/1956 | Cornock et al. | 493/377 X |
| 3,074,467 | 1/1963 | Takats | 156/505 |
| 3,828,367 | 8/1974 | Bourgeois | 156/164 |
| 3,837,975 | 2/1972 | Mandich et al. | 156/513 |
| 4,189,339 | 2/1980 | Loeffler et al. | 156/265 X |
| 4,240,866 | 12/1980 | Rega | 156/552 X |
| 4,261,782 | 4/1981 | Teed | 156/361 |
| 4,284,454 | 8/1981 | Joa | 156/163 |
| 4,285,747 | 8/1981 | Rega . | |
| 4,293,367 | 10/1981 | Klasek et al. | 156/164 |
| 4,297,157 | 10/1981 | Van Vliet | 156/164 X |

Primary Examiner—David Simmons
Attorney, Agent, or Firm—P. A. Leipold; D. L. Traut; J. J. Duggan

[57] ABSTRACT

The invention provides an efficient method and apparatus for applying linear segments of elastic to a base material transverse to the direction the base material is moving in a production line. This object is obtained by providing an apparatus with means for sequentially and repeatedly gripping an elastic strip, pulling that elastic strip across the base material, and then releasing the elastic strip. At about the same time the elastic strip is released, it is cut to size. Also at this same time, the elastic strip is brought into contact with the base material. Preferably, the elastic strip is brought into contact with the base material by virtue of rotation of the gripping, pulling and releasing means.

15 Claims, 10 Drawing Figures

U.S. Patent  Feb. 10, 1987  Sheet 1 of 3  4,642,151
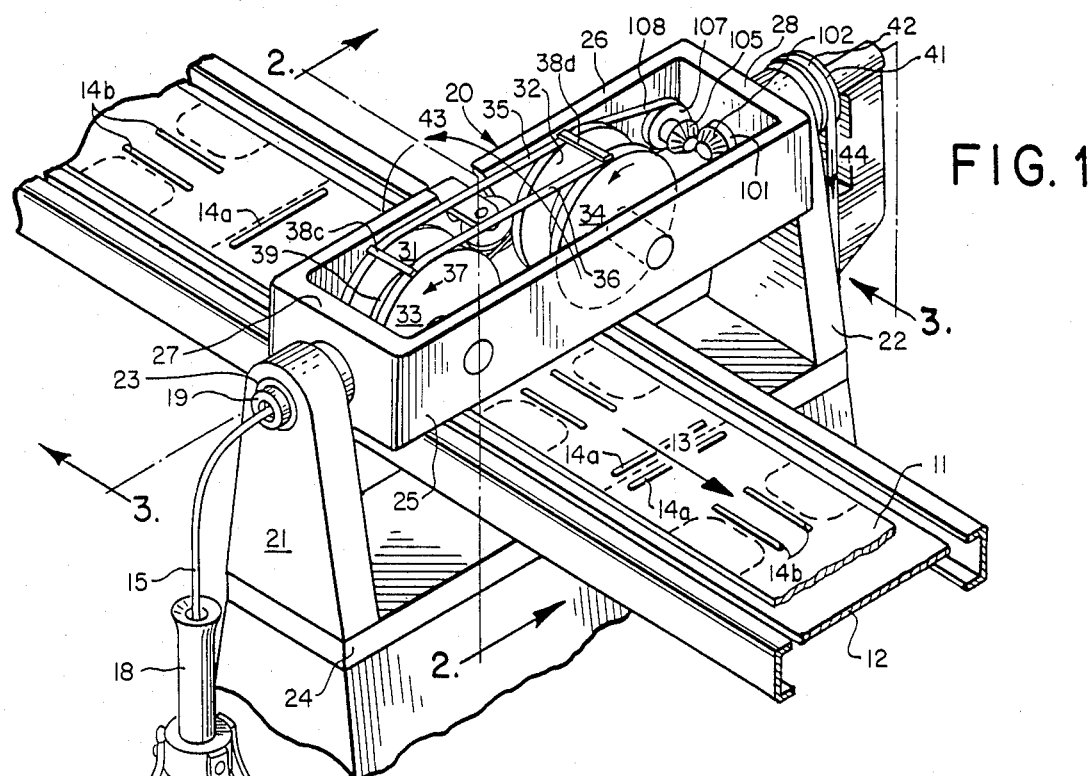
FIG. 1
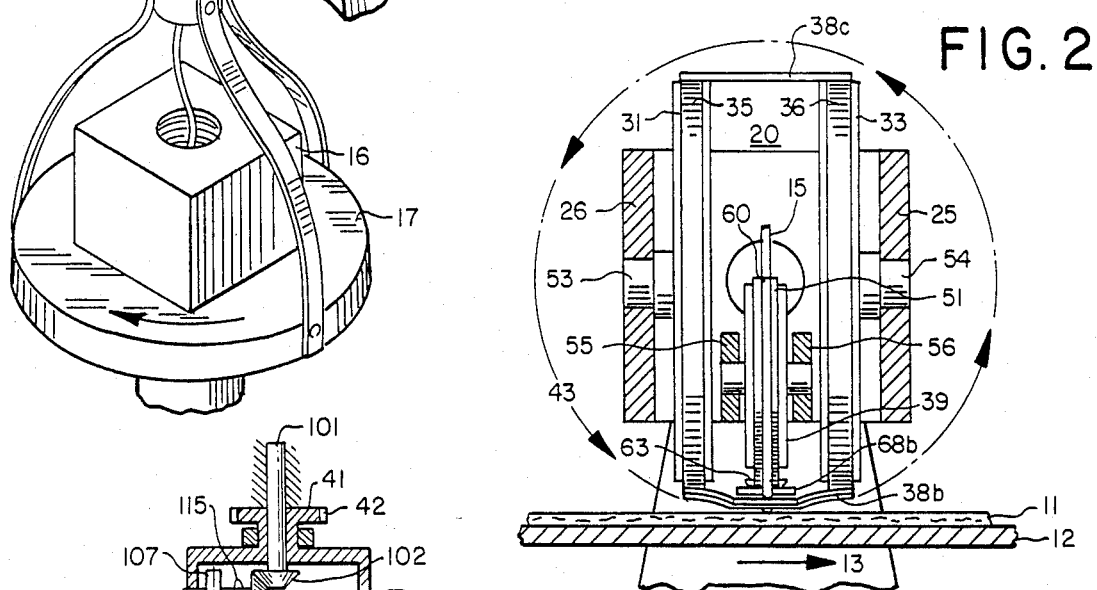
FIG. 2
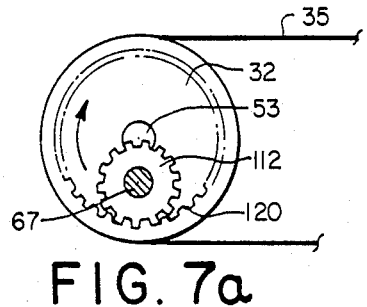
FIG. 7
FIG. 7a

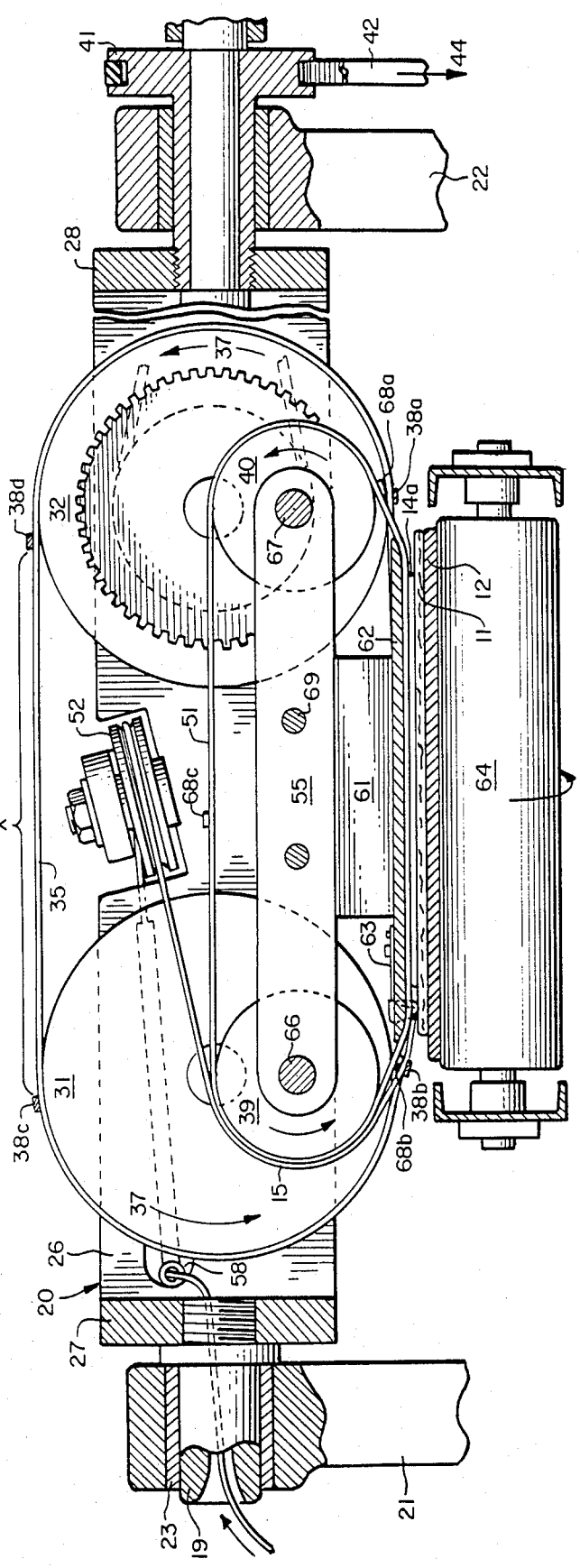

APPARATUS AND METHOD FOR APPLYING TRANSVERSE ELASTIC SEGMENTS

BACKGROUND OF THE INVENTION

1. Field of the Invention

This invention relates generally to methods and apparatuses for applying elastic segments to a base material. More particularly, it concerns the application of elastic segments to a base material in a direction which is transverse to the direction in which the base material is being moved in a production line.

2. Description of the Prior Art

There are a great number of methods and apparatus disclosed in the prior art for applying segments of elastic to a base material. Particularly in the field of disposable garments such as baby diapers and incontinence pads, where production methods must be extremely efficient and economical, there have been several attempts to simplify and speed up the process. Most of these methods are limited to applying the elastic in the same direction as the base material is moving in the production line. For examples, see U.S. Pat. Nos. 4,239,578; 4,297,157; 4,309,236; 4,353,762; 4,360,398; 4,364,787; and 4,371,417. In each of these designs, a strip of elastic is brought in contact with the base material and then be various arrangements of drums and rollers the elastic is attached as the base material moves past, thereby fixing the elastic in the direction the base material is moving.

There exists a need, however, for an efficient method and apparatus to apply elastic segments in a direction transverse to that of the production line. For example, certain garments, such as diapers and incontinence pads, are constructed with elastic segments running in two directions, i.e. for the leg portions and the waist portion. In this example, unless one set of elastic segments is applied followed by a 90° rotation of the garment before applying the second set, a transverse applying design is required. In addition, there may be other factors such as product dimensions and process parameters which make a transverse application desirable.

U.S. Pat. Nos. 3,828,367 and 4,293,367 both describe processes for applying elastic to a moving base material wherein the elastic strip is moved transversely to apply a non-linear elastic segment to the base material. Although these designs are beneficial for some applications, because they both use the travel of the base material to apply the elastic, neither would be suitable for the applications mentioned above.

U.S. Pat. No. 4,240,866, directed to an apparatus, and U.S. Pat. No. 4,285,747 directed to a corresponding method, teach a process for applying elastic segments transverse to the production line travel. The disclosed apparatus is similar to those mentioned above in that it applies the elastic from a roller onto the base material as it passes by. The difference is that short elastic segments are transversely cut from a wide roll of elastic thereby producing a strip which is wide enough to extend across the intended area of application. These wide segments are rotated on an equally wide drum and brought into contact with the moving sheet of base material.

U.S. Pat. No. 4,284,454 also discloses a method for applying elastic segments transversely to a moving base material in manufacturing diapers. This relatively complex apparatus includes a set of cam or piston operated grippers, mounted on an endless chain moving transverse to the production line, which stretch the elastic and move it across the base material. A second set of grippers, mounted on an endless chain moving with the production line, pick up the stretched piece of elastic, apply it to the base material and hold it in place until the remaining layers of the diaper are assembled.

SUMMARY OF THE INVENTION

It is a general object of the present invention to provide an efficient method and apparatus for applying linear segments of elastic to a base material transverse to the direction the base material is moving in a production line. This object is obtained by providing an apparatus with means for sequentially and repeatedly gripping an elastic strip, pulling that elastic strip across the base material, and then releasing the elastic strip. At about the same time the elastic strip is released, it is cut to size. Also at this same time, the elastic strip is brought into contact with the base material. Preferably, the elastic strip is brought into contact with the base material by virtue of rotation of the gripping, pulling and releasing means.

In accord with one embodiment of the invention, the gripping, pulling and releasing means includes an elastic gripping unit comprising a first and second rotating pair of pulleys with a first and second belt mounted thereon. The first belt is longer than the second belt and has at least 3 gripping members attached at equal intervals along the first belt's length. Each pair of pulleys is rotated at a respective angular velocity such that both belts travel at the same linear velocity. The pairs of pulleys are arranged so that upon rotation, an extending portion of the gripping members is brought into and out of contact with the smaller belt. Each gripping member comes into contact with the smaller belt at a point near the start of one of the smaller belt's linear travel sections. The gripping member retains contact along the linear travel section and is brought away from the smaller belt at a point near where the smaller belt begins its travel around one of its pulleys. The present invention makes use of this repeating contact, linear travel, and release of the gripping members to grip an elastic strip, pull it across a predetermined distance, and release it. The invention also comprises a cutting means whereby simultaneously with its release the elastic strip is cut into a segment of predetermined length just after it has been pulled across and gripped again by a trailing gripping member.

The preferred embodiment includes a third pair of pulleys with a third belt mounted thereon. Each of the pulleys in this third pair are of equal size to the corresponding pulleys of the first pair. This third belt is of equal length to the first belt. The second pair of pulleys is located between the first and third. Also, each gripping member is attached to both the first and the third belt.

In this preferred embodiment the second belt also includes three lugs protruding from it. These lugs are each spaced along the second belt at a distance equal to the space between the gripping members on the first belt. The lugs are adapted for being contacted by the gripping members, thereby providing a more positive gripping of the elastic strip.

The preferred embodiment also includes a means for rotating the entire elastic gripping unit about an axis parallel to a line passing through both pulleys of either pair. In this embodiment, the elastic gripping unit is spatially arranged relative to the base material moving below so that the pulled strip of elastic which is held on the second belt is brought into contact with the base material. Additionally, this unit rotation is timed so that the contacting of the base material occurs concurrently with the cutting and releasing of each elastic segment. Also, in this preferred embodiment, the angular velocity of this unit rotation is set so as to produce zero relative velocity between the elastic being applied and the moving base material.

In another embodiment, rather than rotating the entire elastic gripping unit, it is reciprocally moved linearly in the direction and at the velocity of the production line.

In addition, although much of the description has centered on the use of belts and pulleys, the substitution of chains and sprockets is an obvious design choice and thus considerd to be within the scope of the invention as claimed.

BRIEF DESCRIPTION OF THE DRAWINGS

The invention will be more fully described in conjunction with the following drawings wherein:

FIG. 1 is a perspective view of the preferred embodiment of the invention as operated with a moving production line.

FIG. 2 is a sectional view of the preferred embodiment taken along line 2—2 of FIG. 1.

FIG. 3 is a sectional view of the preferred embodiment taken along line 3—3 of FIG. 1.

FIG. 4 is a top view of the preferred embodiment.

FIG. 7 is partial top view of the embodiment depicted in FIGS. 1-4 showing the drive mechanism for the pulleys.

FIG. 7a is a cross section taken along line 7a—7a in FIG. 7 showing the internal gear drive of the smaller pulley.

DETAILED DESCRIPTION

Figure 5A:
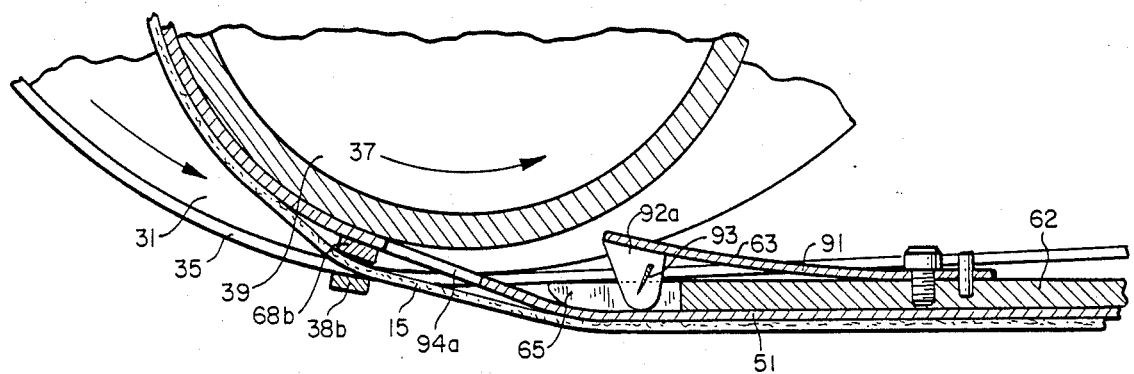
FIGS. 5a-5c are partial sectional views illustrating the sequence of the gripping and cutting operations of the preferred embodiment.

Referring to the drawings, FIG. 1 is a perspective view of the present invention showing its operation of attaching elastic in connection with a production line for disposable diapers. The invention is also suited for operation in connection with the production of other garments such as personal incontinence pads and the like which require an elastic strip. The diaper blanks 11 are moved by a conveyor belt 12 in the direction indicated by arrow 13. These blanks may arrive at this station in various stages of completion. In this depicted embodiment, two pieces of leg elastic 14b and one piece of waist elastic 14a have already been applied to a polyethylene sheet 11 before arriving at this apparatus. This apparatus will apply a second piece of waist elastic 14a. Because this particular garment includes two pieces of waist elastic which are relatively close together it is preferable to utilize two apparatuses of the present invention which are spaced along the conveyor and apply one or the other piece of waist elastic. After receiving the final piece of elastic 14a, the other components are added to form the completed diapers.

In the preferred embodiment, before arriving at this apparatus, adhesive is applied to the sheet 11 at the position where the elastic is to be attached. In another preferred embodiment, an adhesive is applied to the elastic immediately prior to the application of the elastic to the base material. In this other embodiment the adhesive is applied intermittently along the elastic so as to avoid adhesive contact with the gripping members 38a-d. Likewise, a heat activatable adhesive may be incorporated on the elastic and thereafter heat activated before or after application of the elastic to the base material.

After passing through the apparatus of this invention, the blank will have an elastic strip 14a attached in a direction transverse to the movement of the conveyor belt. Also, if the particular article being produced requires more than one transverse elastic strip, or if other design parameters dictate, it may be desirable to provide 2 or more apparatus of this invention which could operate side by side simultaneously.

A continuous elastic strip 15 is provided from a source 16 such as a box. Preferably, the source 16 is mounted on a turntable 17 which rotates at the same angular velocity as the gripping unit 20. The elastic strip 15 passes through a guide tube 18 and through the center of a hollow shaft 19. The hollow shaft 19 is attached to the gripping unit 20 and journals within the sleeve bearing 23 which is fit within a hole in the side support 21. The side supports 21 and 22 are attached to a base support 24.

The elastic gripping unit 20 has side plates 25 and 26 and end plates 27 and 28. Housed within the side and end plates are three pairs of pulleys with belts mounted thereon. There are four large pulleys 31, 32, 33, 34, each of which has an axle journaled within one of the side plates 25 or 26. A belt 35 is mounted on the large pulleys 31 and 32. Likewise, a belt 36 is mounted on the large pulleys 33 and 34. In addition, there is a pair of small pulleys 39 and 40 (shown in FIG. 3) with a belt 51 (shown in FIG. 3) mounted thereon which lie between the two pairs of large pulleys 31, 32, 33, and 34. In the preferred embodiment, both pulleys of each pair are equal in diameter and all four larger pulleys are equal in diameter. In another embodiment, the pairs may include pulleys of different diameters.

By means to be discussed in connection with FIG. 7, the large pulleys 31, 32, 33, and 34 and the small pulleys 39 and 40 are made to rotate in the direction indicated by arrow 37. Attached to both of the belts 35 and 36 are four gripping members 38a, 38b (shown in FIG. 3), 38c and 38d (shown here). These gripping members are attached generally perpendicular to the belts 35 and 36 and are equally spaced along the belts at a distance x which is approximately equal to the length of the elastic segment 14a which is applied to the sheet 11. These gripping members preferably comprise a flexible and slightly elastic material such as ultra high molecular weight polyethylene.

FIG. 2 is a cross section showing the arrangement of the large pulleys 31 and 33 on axles 53 and 54 respectively in relation to the small pulley 39 in the preferred embodiment. All three of these pulleys 31, 33, and 39 along with their respective belts 35, 36, and 51 operate generally in parallel planes. The small pulley 39 and small belt 51 operates between the two large pulleys 31 and 33 with belts 35 and 36. In addition, the pulleys are arranged so that the bottom of each, and thereby the bottom linear portion of the belts' 35, 36, and 51 travel, are generally contained in the same plane which is generally perpendicular to the planes of the pulleys and belts. This spatial arrangement produces the result that upon rotation of the pulleys the gripping members 38a–d periodically contact the smaller belt 51. Also, lugs 68a, 68b (shown here), and 68c are preferably included at equal distances along the smaller belt 51 so as to provide the point of contact on the smaller belt for the gripping members 38a–d. In particular, the distance between the lugs 68a–c is equal to x, the distance between the gripping members 38a–d. Also, the smaller pulley 39 is rotated at an angular velocity so that the smaller belt 51 travels at the same linear speed as the larger belts 35 and 36. As a result, the periodic contacting of the smaller belt 51 by the gripping members is synchronized such that the gripping members always contact the lugs.

The elastic 15 is brought into contact with the smaller belt 51 as that belt is on the pulley 39. At the point of rotation shown in this figure, the strip 15 is pinched between the gripping member 38b and the lug 68b. A guide plate 63 is provided for the smaller belt 51 and is positioned for the smaller belt 51 to ride along its surface across the bottom linear portion of the smaller belt's travel. Also, the guide plate 62 serves to pull the smaller belt 51 slightly below the bottom of the pulley 39. As a result, when the gripping member 38b is flexible, the gripping member bends to compensate for this pulling down of the smaller belt.

In an alternative embodiment, there is only one pair of larger pulleys. In particular, gripping members are provided which are attached to only one belt and extend perpendicularly to contact the smaller belt. Another variation is to not provide lugs on the smaller belt. In this embodiment, the elastic is gripped between the gripping members and the smaller belt.

The arrow 43 shows the direction of the rotation of the gripping unit 20 about the axis 60. This unit rotation is synchronized with the rotation of the pulleys and belts so as to bring the gripped elastic into contact with the article 11 moving on the conveyor belt 12 below. The angular velocity of the unit rotation is also selected in relation to the linear speed of the conveyor 12 so as to minimize the relative velocity between the unit and the article 11 to receive the elastic at the point of contact. In the preferred embodiment, the relative velocity between the elastic and the article 11 is zero at the point of contact. This is highly desirable as it would allow for greater uninterrupted line speeds in the production process.

In an alternative embodiment, instead of rotating the gripping unit to bring the elastic into contact with the article, the gripping unit is repeatedly moved up and down so that the elastic is pushed onto the article at the proper point. In yet another embodiment, the gripping unit is moved on an endless chain in line with the production line for a distance sufficient to allow zero relative velocity between the elastic and then lifted off the article and brought back to a point to apply another segment of elastic. In such an embodiment, it would likely be desirable to have more than one gripping unit on such an endless chain.

FIG. 3 is a cross section showing further the innerworkings of the pulleys and belts in the preferred embodiment of the present invention. The elastic strip 15 is brought through the hollow shaft 19 of the gripping unit 20 and is also led through a guide tube 58. This guide tube 58 passes to the outside of the gripping unit 20 through the side plate 26. The elastic strip 15 leaves the guide tube 58 and comes in contact with the guide pulley 52. This guide pulley 52 is positioned so as to provide the elastic strip onto the smaller belt 51. In addition, this guide pulley preferably is used to impart stretch in the elastic strip 15. In the preferred embodiment, this is done by incorporating a hysteresis brake in the pulley 52. In this way, the elastic is delivered to the article 11 in a stretched state. An alternative method of imparting stretch to the elastic strip is to use an elastic which is applied in a relaxed state and then can be heat activated to produce the stretch.

The elastic strip 15 lies along the surface of the smaller belt 51 and as mentioned before, is gripped between a gripping member such as 38b and a lug on the smaller belt such as 68b.

The sequence for gripping, pulling, applying, cutting, and releasing the elastic strip 15 and the elastic segment 14a can be described as follows. As mentioned, the elastic strip is gripped between one of the lugs 68a–c and one of the gripping members 38a–d. In particular, as a gripping member is brought around to the bottom point of the larger belt's travel, it is also brought into contact with a lug on the smaller belt. When this happens, the elastic which has lain along the smaller belt 51 becomes pinched between the lug and gripping member and is thereby gripped. As the rotation of the belts continues, the gripped elastic strip 15 is pulled across this bottom portion of the belt's travel. When the strip 15 is pulled the entire distance, the gripping unit is brought into contact with the article to receive the elastic. Simultaneously, or very shortly before or after, the elastic is cut by cutting means 63 and also released from the original gripping member and lug, thereby resulting in a stretched segment of elastic 14a being applied to the article 11. The operation and timing of the preferred cutting means is discussed in relation to FIGS. 5a–c and 6. The elastic is released because as the lug begins to move up and around the smaller pulley 40, it lifts off of the gripping member. Also, before the strip is cut, a new gripping member and lug have rotated into position to grip the elastic behind the cut, whereby the elastic strip 15 is always gripped by at least one lug and gripping member.

The smaller pulleys 39 and 40 are mounted on axles 66 and 67 respectively. These axles journal within support plates 55 and 56 (shown in FIG. 4) which is attached to the side plates 25 and 26 by posts 69. Also attached to the support plate 55 is a vertical plate 61 which in turn is attached to a guide plate 62. The guide plate 62 is positioned for the smaller belt 51 to pass along and serves as a support for the smaller belt 51 especially when contacting the article 11. Preferably, the guide plate is positioned slightly below the bottoms of the smaller pulleys 39 and 40. As a result, the smaller belt 51 is pulled down slightly. In addition, because the gripping members 38a–d are preferably flexible, the gripping members are made to bend, as shown in FIG. 2, when resting on a lug on the smaller belt 51 which is riding along the guide plate 62. After the lug passes off the guide plate 62, the gripping member will straighten. These results are desirable as they improve the gripping of the elastic between the gripping members 38a–d and lugs 68a–c. Also, the smaller belt 51 is pushed slightly below the larger belts 35 and 36 so that the elastic held on it can contact the article 11 without the larger belts contacting the article.

In addition to the flexibility and elasticity of the gripping members 38a–d, the larger belts 35 and 36 as well as the smaller belt 51 may be slightly elastic in order to provide better gripping of the elastic and to maintain tension on the belts. It may further be desirable to maintain tension in the belts by providing pre-compressed springs which push one of the axles of each pair of pulleys away from the other pulley.

As can be seen, the preferred embodiment utilizes four gripping members 38a–d on the larger belts 35 and 36 and three lugs 68a–c on the smaller belt 51. Each of these lugs and gripping members are spaced apart from each other a distance x which is approximately equal to the length of the elastic segment 14a to be applied to the article 11. As a result, the larger belts 35 and 36 are 4x in length while the smaller belt is 3x in length. Each pair of larger pulleys as well as the pair of smaller pulleys is spaced approximately a distance of x from center to center. As a result, the circumference of the larger pulleys 31-34 is approximately 2x and the circumference of each of the smaller pulleys 39 and 40 is approximately x.

In alternative embodiments, the number of gripping members on the larger belts as well as the number of lugs on the smaller belt could be varied within certain limitations. First, in an embodiment which includes lugs on the smaller belt, three is the minimum number of lugs and four is the minimum number of gripping members. In an embodiment without lugs, or where the lugs are spaced closer together than the gripping members, three is the minimum number of gripping members. In either embodiment, there may be more than four gripping members on the larger belts and more than three gripping members on the smaller belt. Naturally, there must be at least one more gripping member than lugs if the lugs are spaced at the same distance. Also, because it is important that the distance between the centers of the pairs of pulleys be approximately equal to the distance between the gripping members, the pulleys must be made accordingly larger if there are more than four gripping members or more than three lugs. Alternatively, additional pulleys can be included in the path of the belts in order to accommodate more than four gripping members or more than three lugs.

FIG. 4 is a top view of the gripping unit which also shows the spatial relationships between the pulleys and belts of the preferred embodiment of the present invention.

Figure 5B:
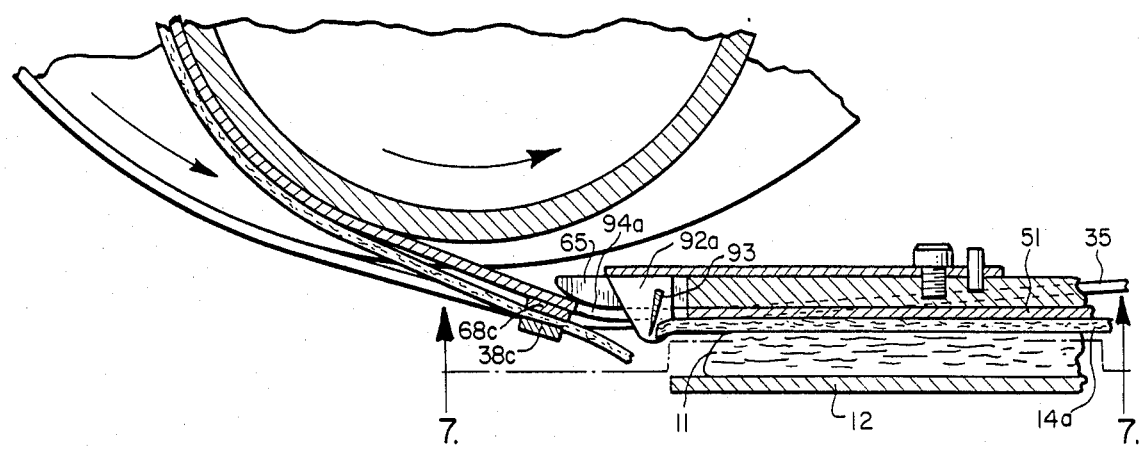
Figure 5C:
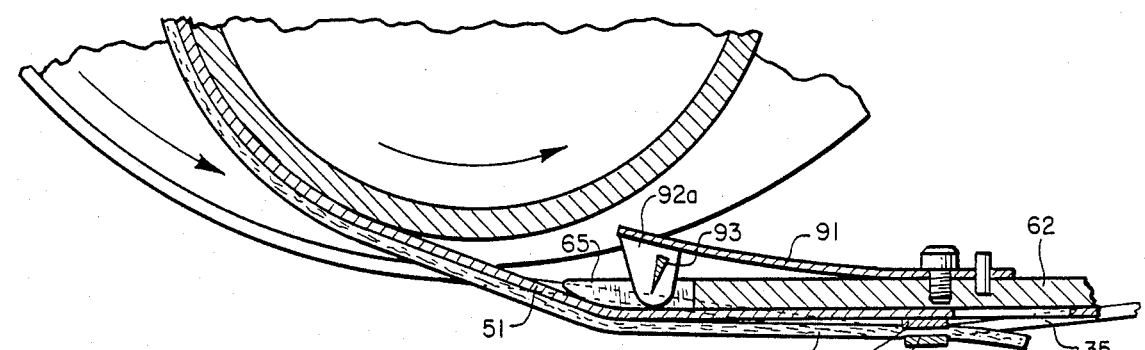

FIGS. 5a through 5c illustrate the gripping and cutting sequence of the preferred embodiment. In FIG. 5a, the gripping member 38b is just beginning to pinch the elastic strip 15 as it lays on the lug 68b on the smaller belt 51. The free end (not shown) of the elastic strip 15 is at this point gripped between the lug 68a and the gripping member 38a. The smaller belt 51 is riding on the guide plate 62. Preferably, the guide plate 62 includes a wear pad 65 made from a material such as teflon.

The cutting means 63 comprises a pre-loaded spring 91 to which is attached the cams 92a and 92b (shown in FIG. 6) and a cutting blade 93. In another embodiment, a resistance heated wire is substituted for the cutting knife which severs the elastic by melting or burning. The cams 92a,b fit through two holes (not shown) in the guide plate 62 and ride along the inner surface of the smaller belt 51. The smaller belt 51 also includes three sets of holes, including the cam holes 94a and 94b, through which the cams 92a,b and the cutting blade 93 can drop.

FIG. 5b illustrates how when the small belt has rotated to the proper point, the cams and cutting blade drop through the smaller belt 51 and cut the elastic strip 15, thus producing the elastic segment 14a. It can also be seen that by this point, the now free end of the elastic strip is fully gripped between the lug 68c and the gripping member 38c.

FIG. 5c shows how the cams with the cutting blade 93 are lifted up after the holes in the smaller belt 51 have passed. In particular, the cams are shaped with a sloped leading edge so that the trailing edges of the holes 94a,b push the cams and thereby the blade on the spring 91 back to its non-cutting position. This figure also shows how the larger belt 35 has been pulled down as the gripping member 38b is in contact with the lug 68b while it is on the guide plate 62.

Figure 6:
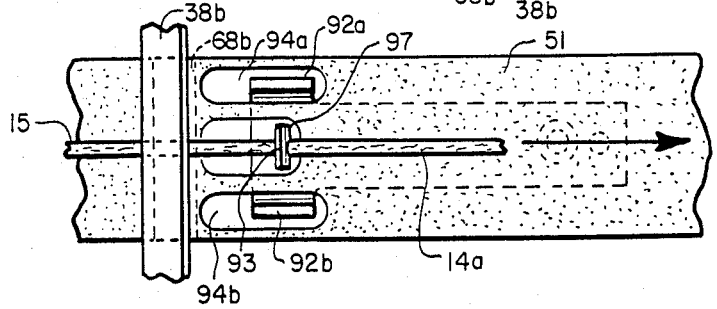
FIG. 6 is a partial bottom view of the preferred embodiment further illustrating the cutting operation.

FIG. 6 is a partial bottom view showing the configuration of the three holes in the smaller belt 51. The cam holes 94a and 94b allow the cams 92a and 92b to drop through the belt 51. As the cams drop, the cutting blade 93 also drops and cuts the elastic strip 15 into an elastic segment 14a. As can be seen, these holes are positioned just ahead of the lug 68b on the small belt 51. In this way, the cutting of the elastic is properly timed to coincide with the release of the other end of the segment 14a and to occur just after the strip 15 has been gripped. Two other sets of holes are also located in the small belt 51, each likewise just ahead of the lugs 68a and 68c.

In an alternative embodiment, instead of holes in the smaller belt, there are bumps on the smaller belt which contact the cams and push the blade or hot wire through the elastic. In yet another embodiment, there is provided a solenoid to move the cutting blade or wire through the elastic. The solenoid can be activated by means of a conducting strip placed on the smaller belt 51 which completes a circuit between two contacts. Naturally, the position of such a conducting strip would provide the timing of the activation of the solenoid and thereby the cutting of the elastic.

FIG. 7 is a sectional top view of the preferred embodiment which illustrates the means for rotating each of the pairs of pulleys. As mentioned, a belt 42 which is mounted on the pulley 41 is driven by motor 44 so as to rotate the gripping unit 20. A shaft 101 is fixed externally to the parent machine 20 and does not rotate. A miter gear 102 on the end of the fixed shaft 101 mates with a miter gear 105 which is on the end of an axle 103. As the gripping unit 20 rotates, the axle 103 is rotated in the direction indicated by arrow 115 by virtue of the contact of its miter gear 105 with the miter gear of the non-rotating shaft 101. Fixed to the axle 103 is a pulley 107 with a belt mounted thereon. The belt is also mounted on a pulley 109 which is fixed to the axle 110 of the large pulley 32. The size of the miter gears as well as the size of the pulleys 107 and 109 are selected so as to produce the proper ratio of revolutions of the gripping unit 20 to revolutions of the large pulley 32. In the preferred embodiment this ratio is 2 to 1, that is the gripping unit should rotate 2 times to every one rotation of the large pulleys.

Referring to FIG. 7a, the large pulley 32 includes an internal gear 120. The axle 67 for the small pulley 40 has a gear 112 on its end which mates with the internal gear 120. As a result, when the larger pulley 32 is rotated, the smaller pulley is rotated in the same direction. The size of the internal gear 120 and the gear 112 are selected so as to provide the proper ratio of revolutions of the smaller pulley 40 to the revolutions of the larger pulley 32. In the preferred embodiment this ratio is 2 to 1.

As can be seen in FIGS. 7 and 7a, the axle 67 for the smaller pulley 40 also has a gear 111 on its other end. This gear mates with an internal gear on the large pulley 34. The gears 111 and 112 are the same size as are the internal gears on each of the large pulleys 32 and 34. As a result, the large pulley 34 is rotated at the same angular velocity as the large pulley 32.

Because of the strict requirements for synchronization of the rotation of each of the belts, it may be desirable in the preferred embodiment to provide holes in the belts, 35, 36, 51 and 108 which would index with protrusions on each of their respective pulleys. Likewise, it may be desirable to use endless chains in the place of one or more of the belts with accompanying use of sprockets in the place of the respective pulleys. Certainly, these and other modifications which will be apparent to one skilled in the art are considered within the scope of the present invention as set out in the following claims.

I claim:

1. An apparatus for applying linear segments of an elastic strip to a base material moving in a production line which comprises:
   a first pair of pulleys with a first belt mounted thereon, and operating generally in a first plane;
   a second pair of pulleys with a second belt mounted thereon, said second pair of pulleys having a combined diameter less than the combined diameter of said first pair, and said second belt having a length less than that of said first belt, said second pair of pulleys and said second belt operating generally in a second plane which is substantially parallel to said first plane;
   at least three gripping members with a first portion attached to said first belt and spaced equally along said first belt, and a second portion extending from said first belt in a direction substantially perpendicular to said first plane;
   means for driving said first pair of pulleys;
   means for driving said second pair of pulleys at a combined angular velocity such that said second belt travels at a linear velocity equal to the linear velocity of said first belt;
   said first pair of pulleys and said second pair of pulleys being arranged such that upon rotation of said first pair of pulleys said second portions of said gripping members are brought into and out of contact with said second belt, and such that at least one of said second portions is in contact with said second belt at all points of said rotation;
   a source of a continuous elastic strip;
   means for guiding said elastic strip from said source to a point in contact with said second belt;
   means for cutting the elastic strip material into linear segments.

2. The apparatus of claim 1 further comprising:
   a third pair of pulleys with a third belt mounted thereon, said third pair of pulleys having a combined diameter equal to the combined diameter of said first pair, said third belt having a length equal to that of said first belt, said third pair of pulleys and said third belt operating generally in a third plane which is parallel to said first plane;
   each of said gripping members further comprising a third portion adjacent to said second portion and attached to said third belt.

3. The apparatus of claim 1 or 2 wherein the second belt further comprises at least three lugs equally spaced along said second belt.

4. The apparatus of claim 3 further comprising a unit rotating means for causing simultaneous rotation of said first and second pair of pulleys and said first and second belts about a single axis of rotation, said axis of rotation being parallel to a line passing through both pulleys of said first pair.

5. The apparatus of claim 4 further comprising means for rotating said source of said elastic strip.

6. The apparatus of claim 1 or 2 further comprising a unit moving means for causing simultaneous movement of said first and second pairs of pulleys and said first and second belts in a direction perpendicular to the linear travel of said second belt.

7. The apparatus of claim 1 or 2, wherein said means for cutting the elastic strip comprises:
   a cutting member;
   an actuating means in contact with said cutting member for moving said cutting member through the elastic strip.

8. The apparatus of claim 7 wherein the actuating means comprises a cam, and one of the belts further comprises at least three protrusions which contact and move said cam thereby moving said cutting member through the elastic strip.

9. The apparatus of claim 7 wherein the actuating means comprises a cam and one of the belts further defines at least three holes into which said cam may drop thereby moving said cutting member through the elastic strip.

10. The apparatus of claim 9, wherein said actuating means further comprises a pre-loaded spring.

11. The apparatus of claim 7, wherein said cutting member comprises a sharp blade.

12. The apparatus of claim 7, wherein said cutting member comprises a resistance heated wire.

13. A method for applying linear elastic segments to a substrate, said method comprising the steps of:
   (a) providing an elastic gripping unit comprising a first pair of pulleys with a first belt mounted thereon; a second pair of pulleys with a second belt mounted thereon, said second pair of pulleys having a combined diameter less than that of said first pair, said second belt having a length less than that of said first belt; at least three gripping members attached to said first belt and extending therefrom; said first and second pair of pulleys spatially arranged so that upon rotation of said first pair of pulleys, the gripping members are brought into and out of contact with said second belt;
   (b) providing a continuous elastic strip;
   (c) providing a cutting means whereby said continuous elastic strip is cut into segments;
   (d) rotating said first and second pairs of pulleys at respective angular velocities such that said first and second belts travel at the same linear velocity;
   (e) guiding the continuous elastic strip to a point in contact with said second belt;
   (f) gripping a portion of the continuous elastic strip between one of said gripping members and the second belt;
   (g) pulling the gripped portion of the continuous elastic material in a direction transverse to the direction of the production line by continued rotation of said first and second pairs of pulleys;
   (h) bringing the pulled portion of the continuous elastic material into contact with said substrate;
   (i) cutting said continuous elastic strip into a segment of desired length;
   (j) releasing the segment from between said one of said gripping members and said second belt by continued rotation of said first and second pairs of pulleys.

14. The method of claim 13 wherein the continuous elastic strip is brought into contact with the substrate by:

rotating the elastic gripping unit about an axis of rotation which is parallel to a line passing through both pulleys of said first pair;

arranging the elastic gripping unit in spatial relation to the substrate such that, upon said rotation of said elastic gripping unit, the pulled portion of the continuous elastic strip is brought into contact with said substrate;

said rotation of the elastic gripping unit being synchronized with said respective rotations of the first and second pairs of pulleys such that the contact with said substrate occurs just after the elastic strip has been pulled and just before it is cut and released.

15. The method of claim 13, wherein the angular velocity of the rotation of the elastic gripping unit is selected so as to provide zero relative velocity between the substrate moving in the production and the elastic strip when brought into contact with said substrate.

* * * * *